United States Patent
Stock et al.

(10) Patent No.: US 7,993,281 B2
(45) Date of Patent: Aug. 9, 2011

(54) BREATH ALCOHOL MEASURING DEVICE WITH IMPROVED MOUTHPIECE

(75) Inventors: Burkhard Stock, Lübeck (DE); Jens Rekow, Lübeck (DE); Rigobert Chrzan, Bad Oldesloe (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1379 days.

(21) Appl. No.: 11/420,629

(22) Filed: May 26, 2006

(65) Prior Publication Data

US 2006/0206034 A1    Sep. 14, 2006

Related U.S. Application Data

(63) Continuation of application No. 10/802,296, filed on Mar. 17, 2004, now abandoned.

(30) Foreign Application Priority Data

Apr. 10, 2003 (DE) .................. 103 16 333

(51) Int. Cl.
*A61B 5/08* (2006.01)
*G01N 33/497* (2006.01)
(52) U.S. Cl. ............ 600/532; 600/529; 73/23.3
(58) Field of Classification Search ......... 600/529–543; 73/23.3
See application file for complete search history.

(56) References Cited

U.S. PATENT DOCUMENTS

| | | | | |
|---|---|---|---|---|
| 3,797,479 A * | 3/1974 | Graham | .................. | 600/538 |
| 3,880,591 A * | 4/1975 | Burroughs | ............. | 600/529 |
| 3,946,726 A * | 3/1976 | Pikul | ..................... | 600/538 |
| 4,122,842 A * | 10/1978 | Pikul | ..................... | 600/538 |
| 4,297,871 A * | 11/1981 | Wright et al. | ............ | 73/23.3 |
| 4,564,021 A * | 1/1986 | Siegmann et al. | ......... | 600/529 |
| 4,707,336 A * | 11/1987 | Jones | ...................... | 422/84 |
| 4,744,953 A * | 5/1988 | Wolf et al. | .............. | 422/84 |
| 4,868,545 A * | 9/1989 | Jones | .................... | 340/573.1 |
| 4,905,709 A * | 3/1990 | Bieganski et al. | ......... | 600/538 |
| 4,981,295 A * | 1/1991 | Belman et al. | ............. | 482/13 |
| 5,111,827 A * | 5/1992 | Rantala | ................... | 600/532 |
| 5,137,026 A * | 8/1992 | Waterson et al. | ......... | 600/538 |
| 5,291,898 A * | 3/1994 | Wolf | ...................... | 600/532 |
| 5,458,853 A * | 10/1995 | Porter et al. | .............. | 422/84 |
| 5,501,231 A * | 3/1996 | Kaish | ..................... | 600/538 |
| 5,518,002 A * | 5/1996 | Wolf et al. | ............... | 600/538 |
| 5,564,432 A * | 10/1996 | Thomson | ................ | 600/538 |
| 5,715,831 A * | 2/1998 | Johnson | ................. | 600/539 |
| 5,735,287 A * | 4/1998 | Thomson | ................ | 600/538 |
| 5,739,412 A * | 4/1998 | Stock et al. | ............... | 73/23.3 |
| 5,743,270 A * | 4/1998 | Gazzara et al. | ........... | 600/539 |
| 5,789,660 A * | 8/1998 | Kofoed et al. | ............ | 73/23.2 |
| 5,980,466 A * | 11/1999 | Thomson | ................ | 600/538 |
| 5,997,483 A * | 12/1999 | Johnson | ................. | 600/538 |
| 6,044,843 A * | 4/2000 | O'Neil et al. | ............ | 128/204.23 |
| 6,113,549 A * | 9/2000 | Johnson | ................. | 600/529 |
| 6,176,833 B1 * | 1/2001 | Thomson | ................ | 600/538 |
| 6,190,326 B1 * | 2/2001 | McKinnon et al. | ........ | 600/529 |
| 6,190,327 B1 * | 2/2001 | Isaacson et al. | .......... | 600/529 |

(Continued)

*Primary Examiner* — Charles A Marmor, II
*Assistant Examiner* — Navin Natnithithadha
(74) *Attorney, Agent, or Firm* — McGlew and Tuttle, P.C.

(57) ABSTRACT

A breath alcohol measuring device (7) is provided with features for superior handling especially of the replaceable mouthpiece (1). A direct physical contact between the test subject being tested and the measuring device is practically ruled out by the combination. The mouthpiece (1) of the breath alcohol measuring device (7) has a trapezoidal cross section, which is complementary to a corresponding negative shape in a holder (6) of the breath alcohol measuring device (7) for the flush mounting of the mouthpiece (1).

22 Claims, 1 Drawing Sheet

U.S. PATENT DOCUMENTS

| | | | |
|---|---|---|---|
| 6,325,978 B1* | 12/2001 | Labuda et al. | 422/84 |
| 6,367,475 B1* | 4/2002 | Kofoed et al. | 128/205.23 |
| 6,468,222 B1* | 10/2002 | Mault et al. | 600/531 |
| 6,824,520 B2* | 11/2004 | Orr et al. | 600/529 |
| 6,899,683 B2* | 5/2005 | Mault et al. | 600/531 |
| 2004/0204655 A1* | 10/2004 | Stock et al. | 600/532 |
| 2004/0260194 A1* | 12/2004 | Bayer et al. | 600/529 |
| 2006/0206034 A1* | 9/2006 | Stock et al. | 600/532 |

\* cited by examiner

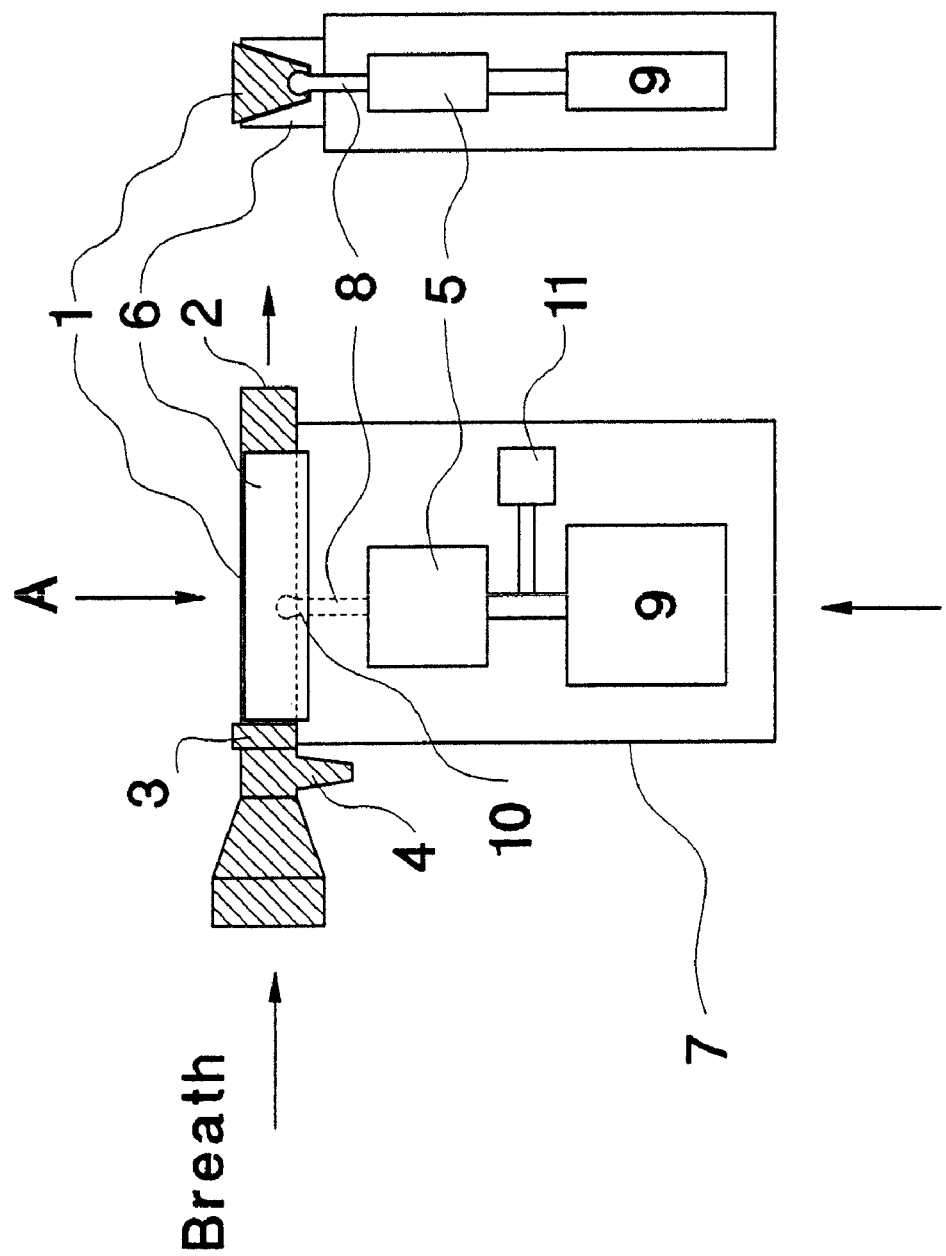

BREATH ALCOHOL MEASURING DEVICE WITH IMPROVED MOUTHPIECE

CROSS REFERENCE TO RELATED APPLICATIONS

This application is a continuation of, and claims the benefit of priority under 35 U.S.C. §120 of, application Ser. No. 10/802,296 filed Mar. 17, 2004 now abandoned, the entire contents of which are incorporated herein by reference. The Ser. No. 10/802,296 application claims the benefit of priority under 35 U.S.C. §119 of German application 103 16 333.6 filed Apr. 10, 2003, the entire contents of which are incorporated herein by reference.

FIELD OF THE INVENTION

The present invention pertains to a breath alcohol measuring device with a mouthpiece designed as a pressure tube with a hole for sampling breathing gas for an alcohol sensor.

BACKGROUND OF THE INVENTION

A breath alcohol measuring device of this type has become known from DE 195 45 794 C2, in which the breathing gas flow within the mouthpiece is split into a main gas stream flowing directly to the environment and a measuring gas stream. The measuring gas stream is sent through the sampling system of the device and set due to the design embodiment of the device in terms of the flow volume to a value that corresponds to that delivered by prior-art calibrating devices, so that calibration of the sampling system is possible under real flow conditions. The drawback of this prior-art measuring device is the lack of hygiene and the condensation of the breathing gas stream during the direct flow of the split measuring gas stream through the sampling system.

Another breath alcohol measuring device of this type is disclosed in EP 0 153 883 A2, in which it is especially difficult to attach the mouthpiece with circular cross section to the measuring device.

SUMMARY OF THE INVENTION

The basic problem that the present invention addresses is that the mouthpiece must be changed for each test subject in breath alcohol measuring devices for hygienic reasons. This operation should be as simple and rapid as possible, because it is often necessary to test many test subjects with one measuring device in a short time, especially at night under unfavorable light conditions in the case of use by the police. The mouthpiece must have a reliable connection with the measuring device during the measurement so that it will not separate during the measurement. Furthermore, it should be ensured for hygienic reasons that the exhaled breathing gas is fed in the mouthpiece only and does not come into contact with the interior of the measuring device. The test subject should have direct contact with the replaceable mouthpiece only during the release of the breathing gas sample and the test subject should not touch the measuring device with lips of the test subject.

Thus, the object of the present invention is to provide a breath alcohol measuring device that is substantially improved in terms of its handling and especially the replaceable mouthpiece. At the same time, the direct physical contact between the test subject being tested as well as the exhaled breathing gas sample and the breath alcohol measuring device shall be practically ruled out with the present invention.

According to the invention, a breath alcohol measuring device is provided with a mouthpiece designed as a pressure tube with a hole for sampling breathing gas for an alcohol sensor. The mouthpiece has a trapezoidal cross section, which is complementary to a corresponding negative shape in the holder of the breath alcohol measuring device. This allows for a flush mounting of the mouthpiece.

The handling of the breath alcohol measuring device in terms of the replacement and the mounting of the replaceable mouthpiece in the measuring device is substantially simplified by means of the present invention, which can be attributed especially to a tapered trapezoidal cross section of the mouthpiece with the fitting negative shape of the complementary holder at the measuring device. A tapered trapezoid shape guides the mouthpiece into the correct position, even if the pieces are slightly misaligned at first.

An especially preferred embodiment of the present invention is characterized in that the trapezoidal cross section of the mouthpiece is equilateral, and the hole in the mouthpiece for breathing gas sampling is located in the shorter of the two parallel sides of the cross section of the mouthpiece. Another preferred embodiment is characterized in that the mouthpiece has a stop, which extends over at least some sections circumferentially in the circumferential direction of the cross section and which sets the correct position of the mouthpiece in the longitudinal direction relative to the holder, so that the suction channel of the measuring device extends exactly through the hole of the mouthpiece for taking a breathing gas sample.

An exemplary embodiment of the present invention will be explained in greater detail below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

FIG. 1 is a schematic view of a breath alcohol measuring device according to the invention; and FIG. 2 is a vertical sectional view taken along the line A-B of FIG. 1.

DESCRIPTION OF THE PREFERRED EMBODIMENT

Referring to the drawings in particular, FIG. 1 shows the view of a breath alcohol measuring device 7. Similar such measuring devices are available commercially especially under the trademark Alcotest®. The replaceable mouthpiece 1 is inserted into a U-shaped holder 6 and is made of, e.g., a plastic such as polyethylene. The U-shaped holder 6 has two leg portions with interior surfaces and a base portion. The interior surfaces of the leg portions taper inward toward the base portion. The mouthpiece 1 has a sample hole 10, through which the suction channel 8 extends into the breathing gas stream (breath stream) blown in from the left as indicated by the arrow in FIG. 1. The pump 9 is actuated such that it delivers a breathing gas sample from the breathing gas stream into the measuring device and consequently into the alcohol sensor 5 by means of a sampling stroke when the test subject has blown a sufficient volume of breathing gas through the mouthpiece 1. The blow-in opening of the mouthpiece 1 is expanded in a circular pattern in order to make possible a good closure with the lips. The mouthpiece 1 also has an attachment portion with a tapered trapezoidal, or tapered U-shape cross section as can be seen in FIG. 2. The trapezoidal cross section of the mouthpiece 1 is complementary to a corresponding negative shape in the holder 6 of the breath alcohol measuring device 7. The trapezoidal cross section of the mouthpiece 1 is preferably equilateral, and the hole 10 for sampling breathing gas is located in the shorter of the two parallel sides of the cross section as can be seen in FIG. 2.

A blow-out opening 2 with a diameter of about 4 mm to 5 mm is located at the outlet-side end of the mouthpiece 1, which is the right-hand end in FIG. 1. The mouthpiece 1 has a mouth diametrically opposite the blow-out opening 2.

As a result, the breathing gas stream generates a dynamic pressure, which is detected by means of the pressure sensor 11. The measured pressure corresponds to a certain breathing gas volume flow, from which the volume of breathing gas released is determined by time integration.

The mouthpiece 1 has the cross section described at least in the area of the holder 6. The upper parallel side (parallel to the lower side) has a length of about 9 mm. The lower parallel side (parallel to the upper side) has a length of about 4 mm. The height of the trapezoid is about 10 mm. The holder 6 is designed as a negative shape to the shape of the mouthpiece 1. FIGS. 1 and 2 show the longitudinal and transverse dimensions, respectively, of the measuring device. As shown in the drawings, the longitudinal length of the holder 6 is several times longer than a transverse length of the holder 6. The mouthpiece can be guided securely on the three lateral or outer surfaces that are complementary to the holder 6 and it is as a result firmly seated in the holder 6. Furthermore, the tapered trapezoidal cross-sectional shape of the mouthpiece 1 facilitates the attachment to the holder 6, so that the suction channel 8 extends through the hole 10 as desired. The tapered trapezoid especially facilitates the firm seating and attachment by the angle of the taper. The orientation of the mouthpiece 1 in relation to the measuring device is thus defined unambiguously.

Furthermore, an external stop 3 extending circumferentially over at least some sections is present, in particular, in the circumferential direction of the cross section of the mouthpiece 1 for the lateral position of the mouthpiece 1 in the holder 6, so that the mouthpiece 1 fits the holder 6 in a completely fitting manner only when the suction channel 8 extends through the hole 10. The stop 3 thus defines the correct lateral position of the mouthpiece 1 in relation to the holder 6. The positioning pin 4, which is optionally present, is used, on the one hand, as an aid for the correct orientation of the mouthpiece 1 for being received in the holder 6, especially in a circumferential angular position, and also when the mouthpiece 1 is still packaged, e.g., in a transport film. The positioning pin 4 is especially useful in the case of unfavorable light conditions during use for measurement and because the mouthpiece 1 still has to be partially packaged in the contact area for hygienic reasons during the attachment to the holder 6 by the user. In addition, the positioning pin 4 acts as a spacer for the test subject, so that contact between the measuring device and the test subject's lips is prevented from occurring.

Breath alcohol measuring device 7 itself has a sensor housing with a parallelepipedic form. The mouth piece 1 is received in the holder 6 extending in parallel to one of the shorter end faces of the parallelepipedic form.

According to a preferred embodiment, the mouthpiece 1 and the holder 6 are symmetrical in relation to the breath alcohol measuring device 7, so that the mouthpiece 1 can be received in the holder 6 in two different positions differing from each other by 180°, and an additional improvement of the handling of the mouthpiece 1 is thus made possible.

While a specific embodiment of the invention has been shown and described in detail to illustrate the application of the principles of the invention, it will be understood that the invention may be embodied otherwise without departing from such principles.

What is claimed is:

1. A breath alcohol measuring device, comprising:
   a holder defining a groove with flat receiving surfaces on opposite longitudinal sides of said groove, said flat receiving surfaces tapering inwardly in a straight line toward a base of said groove;
   an alcohol sensor connected to said holder;
   a mouthpiece designed as a pressure tube with a hole for sampling breathing gas for said alcohol sensor, the mouthpiece having an attachment cross section defining flat outer surfaces that are complementary to a corresponding negative shape of said flat receiving surfaces in said holder, said outer surfaces and said receiving surfaces defining operative fixing means for a flush mounting of said mouthpiece to said holder and for holding said mouthpiece to said holder, said mouthpiece having a stop extending outside said holder when said attachment section is in said holder, said stop extending in a circumferential direction of the attachment cross section over at least some sections of said attachment cross section, said stop setting a position of said mouthpiece in the longitudinal direction in relation to said holder for alignment of an extending suction channel for sampling breathing gas to said hole.

2. A breath alcohol measuring device in accordance with claim 1, wherein the attachment cross section of the mouthpiece is an equilateral trapazoid, and said hole for taking a breath sample is located in a shorter of two parallel sides of the cross section of the mouthpiece.

3. A breath alcohol measuring device in accordance with claim 1, further comprising: a sensor housing having a parallelepipedic form and said mouthpiece is received in said holder extending in parallel to one of two shorter end faces of the parallelepipedic form of said sensor housing.

4. A breath alcohol measuring device in accordance with claim 1, wherein said mouthpiece has a positioning pin, which is arranged outside said holder when the mouthpiece is mounted in said holder.

5. A breath alcohol measuring device in accordance with claim 1, wherein the alcohol sensor includes an electrochemical alcohol sensor in flow connection with said suction channel and a pump, wherein the breathing gas is sampled by means of a sampling stroke of said pump, said pump being arranged downstream of said electrochemical alcohol sensor with the breathing gas being drawn through said electrochemical alcohol sensor.

6. A breath alcohol measuring device in accordance with claim 1, wherein said holder and said mouthpiece are symmetrical in relation to the breath alcohol measuring device whereby said mouthpiece can be mounted in said holder without a preferred direction in two different positions forming an angle of 180° with each other.

7. A breath alcohol measuring device comprising:
   a mouthpiece with a breathing gas passage with a sampling hole for sampling breathing gas, the mouthpiece including a portion with outer surfaces with a trapezoidal shape including angled outer side surfaces, said angled outer side surfaces being flat, non-parallel and on diametrically opposite sides of said mouthpiece and being angled inwardly in a straight line toward a side of said mouthpiece between said angled outer side surfaces;
a sensor housing with a suction channel;
an alcohol sensor arranged in said sensor housing and in communication with said breathing gas passage;
a holder connected to said sensor housing, said holder defining a groove with open longitudinal ends, said groove having angled holder side surfaces cooperating with a holder base surface to provide a partial trapezoidal shape with said holder side surfaces being flat, non-parallel and substantially complementary to said outer side surfaces, said angled holder side surfaces engaging said angled outer side surfaces for firmly seating said mouthpiece into said holder to hold said outer side surfaces in position relative to said holder side surfaces.

8. A breath alcohol measuring device in accordance with claim 7, wherein:
said mouthpiece includes a stop arranged to abut one of said longitudinal ends of said groove when said mouthpiece is arranged in said holder and said sampling hole is in communication with said suction channel.

9. A breath alcohol measuring device in accordance with claim 8, wherein:
said mouthpiece, said stop and said holder are arranged for said stop to abut either one of said longitudinal ends when said mouthpiece is arranged in said holder and said sampling hole is in communication with said suction channel.

10. A breath alcohol measuring device in accordance with claim 7, wherein:
said gas passage in said mouthpiece extends substantially parallel to said groove.

11. A breath alcohol measuring device in accordance with claim 7, wherein:
said mouthpiece longitudinally extends beyond said holder and said housing in both longitudinal directions.

12. A breath alcohol measuring device in accordance with claim 7, wherein:
said trapezoidal shape is a tapered trapezoidal shape;
said trapezoidal shape of said mouthpiece facilitates attachment to said holder.

13. A breath alcohol measuring device in accordance with claim 7, wherein:
said mouthpiece includes a positioning pin arranged to block lips of a user blowing into the mouthpiece from contacting said housing.

14. A breath alcohol measuring device comprising:
a sensor housing defining a suction channel;
an alcohol sensor arranged in said sensor housing and in communication with said suction channel;
a holder arranged on a mounting side of said sensor housing, said holder having a U-shaped receiving portion, said U-shaped receiving portion having two leg portions with interior surfaces and a base portion between ends of said two leg portions, said interior surfaces of said leg portions tapering inwardly toward said base portion, said base portion also defining a suction channel in communication with said suction channel of said sensor housing, said U-shaped receiving portion defining an opening diametrically opposite said base portion, said opening being between other ends of said two leg portions;
a mouthpiece mountable in said U-shaped receiving portion, said mouthpiece defining a breathing gas passage and defining a sample hole for communicating said breathing gas passage with said suction channel, the mouthpiece including an attachment portion with tapered outer surfaces shaped for attachment with said interior surfaces of said two leg portions and said base portion of said U-shaped receiving portion, said attachment portion, said sample hole and said suction channel being arranged to all be in communication with each other when said mouthpiece is mounted in said U-shaped receiving portion, said mouthpiece including a stop separate from said attachment portion, said stop cooperating with said receiving portion to longitudinally align said sample hole with said suction channel when said mouthpiece is inserted into said opening of said U-shaped receiving portion, said tapered outer surfaces of said mouthpiece and said interior surfaces of said U-shaped receiving portion being shaped to guide said mouthpiece into circumferential angular alignment of said sample hole with said suction channel when said mouthpiece is inserted into said opening of said U-shaped receiving portion.

15. A breath alcohol measuring device in accordance with claim 14, wherein:
said attachment portion of the mouthpiece is a tapered trapezoid;
said sample hole for taking a breath sample is located in a shorter of two parallel sides of said tapered trapazoid of the mouthpiece.

16. A breath alcohol measuring device in accordance with claim 14, wherein:
a taper angle of said interior surfaces of said leg portions, and a taper angle of said tapered outer surfaces of said attachment portion create attachment of said mouthpiece to said holder.

17. A breath alcohol measuring device in accordance with claim 14, wherein:
said mouthpiece is mountable in said holder in two longitudinally different angular positions, said sample hole being in communication with said suction channel in both of said longitudinally different angular positions;
said sensor housing is a parallelepiped with a plurality of differently sized sides, said mounting side of said sensor housing being one of two smaller sizes of said plurality of different sized sides of said sensor housing;
said holder receiving said mouthpiece with a longitudinal axis of said mouthpiece being substantially parallel to a longitudinal axis of said mounting side in both of said longitudinally different angular positions;
said mouthpiece having a mouth end extending beyond said mounting side of said sensor housing when said mouthpiece is mounted in said holder and said sample hole is aligned with said suction channel in both of said longitudinally different angular positions.

18. A breath alcohol measuring device in accordance with claim 14, wherein:
said mouthpiece includes a positioning pin extending radially outwards from said mouthpiece, said positioning pin cooperating with said sensor housing to indicate an angular circumferential position for said mouthpiece to be inserted into said holder and align said sample hole with said suction channel, said positioning pin being arranged to block lips of a user blowing into the mouthpiece from contacting said sensor housing.

19. A breath alcohol measuring device in accordance with claim 14, wherein:
said U-shaped receiving portion has a longitudinal length in a longitudinal direction of said holder and said mouthpiece, said longitudinal length being several times longer than a transverse length of said U-shaped receiving portion.

20. A breath alcohol measuring device in accordance with claim 14, wherein:

said sensor housing is a parallelepiped with a plurality of differently sized sides, said mounting side of said sensor housing being one of two smaller sizes of said plurality of different sized sides of said sensor housing;

said holder receiving said mouthpiece with a longitudinal axis of said mouthpiece being substantially parallel to a longitudinal axis of said mounting side;

said mouthpiece having a mouth end extending beyond said mounting side of said sensor housing when said mouthpiece is mounted in said holder and said sample hole is aligned with said suction channel.

21. A breath alcohol measuring device in accordance with claim 14, wherein:

said sample hole and said suction channel are arranged to all be in communication with each other when said mouthpiece is mounted in a correct longitudinal position and a correct angular position in said U-shaped receiving portion, said tapered outer surfaces of said mouthpiece and said interior surfaces of said U-shaped receiving portion are arranged to guide said mouthpiece into said correct angular position when said mouthpiece is inserted into said opening of said U-shaped receiving portion;

said stop aligns said mouthpiece into said correct longitudinal position when said mouthpiece is inserted into said opening of said U-shaped receiving portion.

22. A breath alcohol measuring device in accordance with claim 14, wherein:

said U-shaped receiving portion extends longitudinally in a groove shape with open longitudinal ends;

said interior surfaces of said U-shaped receiving portion, and said outer surfaces of said attachment portion are flat.

* * * * *